United States Patent
St. Pierre

(10) Patent No.: US 10,616,740 B2
(45) Date of Patent: *Apr. 7, 2020

(54) WIRELESS AMBULATORY CARE NETWORK

(71) Applicant: Welch Allyn, Inc., Skaneateles Falls, NY (US)

(72) Inventor: Shawn C. St. Pierre, Syracuse, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 65 days.

This patent is subject to a terminal disclaimer.

(21) Appl. No.: 15/887,713

(22) Filed: Feb. 2, 2018

(65) Prior Publication Data

US 2018/0227733 A1     Aug. 9, 2018

Related U.S. Application Data

(63) Continuation of application No. 14/529,510, filed on Oct. 31, 2014, now Pat. No. 9,924,298.

(51) Int. Cl.
*H04B 7/00*     (2006.01)
*H04W 4/80*     (2018.01)
(Continued)

(52) U.S. Cl.
CPC ............. *H04W 4/80* (2018.02); *A61B 5/0022* (2013.01); *H04W 8/005* (2013.01); *H04W 76/14* (2018.02); *A61B 5/0002* (2013.01)

(58) Field of Classification Search
CPC ....... H04W 4/80; H04W 76/14; H04W 8/005; H04L 67/104; H04L 67/306
(Continued)

(56) References Cited

U.S. PATENT DOCUMENTS

| 8,117,046 B2 * | 2/2012 | Bayne | A61B 5/411 |
| | | | 705/3 |
| 8,634,349 B1 * | 1/2014 | Shmidt | H04W 4/08 |
| | | | 370/328 |

(Continued)

FOREIGN PATENT DOCUMENTS

| CN | 202843955 U | 4/2013 |
| WO | 2013103342 A1 | 7/2013 |

OTHER PUBLICATIONS

"Bluetooth SIG focus on medical / healthcare," Insisor news from Bluetooth™ and short range RF environment, Issue 95, Jun. 2006, 25 pages.

(Continued)

*Primary Examiner* — April G Gonzales
(74) *Attorney, Agent, or Firm* — Merchant & Gould P.C.

(57) ABSTRACT

A method for connecting wireless devices using Bluetooth® low energy can be used to connect wireless computing devices with a medical device in an ambulatory care setting. The wireless computing devices can receive measured vital sign data and transmit the vital sign data to a patient's electronic medical record. The wireless computing devices can be configured to include a user-friendly name and the transmitter power in one or more advertising broadcasts. The medical device can receive advertising broadcasts from one or more wireless computing devices and sort the devices by proximity, last use, number of times used, or alphabetically. After the devices exchange information over Bluetooth® low energy, the devices can connect in Bluetooth® Classic. Systems for implementing the method are also disclosed.

20 Claims, 7 Drawing Sheets

(51) Int. Cl.
*H04W 76/14* (2018.01)
*A61B 5/00* (2006.01)
*H04W 8/00* (2009.01)

(58) Field of Classification Search
USPC .............................................. 455/41.1, 41.2
See application file for complete search history.

(56) References Cited

U.S. PATENT DOCUMENTS

| | | | | |
|---|---|---|---|---|
| 8,645,424 | B2* | 2/2014 | Miller | G06F 19/3418 707/783 |
| 8,682,692 | B2* | 3/2014 | Morris | G16H 10/60 705/2 |
| 8,965,411 | B1* | 2/2015 | Busch-Sorensen | G01S 5/14 455/456.3 |
| 2005/0086377 | A1* | 4/2005 | Aso | H04L 29/12066 709/245 |
| 2006/0046709 | A1* | 3/2006 | Krumm | H04N 21/4126 455/422.1 |
| 2007/0185390 | A1* | 8/2007 | Perkins | A61B 5/0002 600/300 |
| 2008/0139891 | A1* | 6/2008 | Whitehead | G16H 40/20 600/300 |
| 2008/0242365 | A1* | 10/2008 | Rokusek | H04M 1/6075 455/41.2 |
| 2008/0294462 | A1* | 11/2008 | Nuhaan | G06Q 10/063114 705/3 |
| 2010/0029255 | A1* | 2/2010 | Kim | G06F 1/1626 455/414.2 |
| 2010/0041968 | A1* | 2/2010 | Meschisen | G06F 19/321 600/301 |
| 2011/0172550 | A1* | 7/2011 | Martin | A61B 5/7445 600/523 |
| 2012/0058754 | A1* | 3/2012 | Couse | H04M 1/7253 455/416 |
| 2012/0277543 | A1* | 11/2012 | Homchowdhury | A61B 5/002 600/300 |
| 2012/0302910 | A1* | 11/2012 | Freeman | A61N 1/3987 600/538 |
| 2013/0109315 | A1* | 5/2013 | Polo | H04W 52/0274 455/41.2 |
| 2013/0144536 | A1* | 6/2013 | Baker | A61B 5/7203 702/19 |
| 2013/0144790 | A1* | 6/2013 | Clements | G16H 10/60 705/51 |
| 2013/0296719 | A1* | 11/2013 | Packer | A61B 5/0205 600/484 |
| 2013/0317848 | A1* | 11/2013 | Savin | G06Q 10/10 705/3 |
| 2014/0157135 | A1* | 6/2014 | Lee | H04W 76/14 715/738 |
| 2014/0274033 | A1* | 9/2014 | Smart | H04W 52/028 455/426.1 |
| 2014/0323048 | A1* | 10/2014 | Kang | H04W 4/80 455/41.2 |
| 2015/0184401 | A1* | 7/2015 | Steck | E05D 1/02 182/222 |
| 2015/0303091 | A1* | 10/2015 | Ruda Y Witt | H01L 21/68 414/784 |
| 2015/0373091 | A1* | 12/2015 | Sanghavi | H04W 4/80 709/204 |
| 2016/0080888 | A1* | 3/2016 | Kreitzer | H04B 1/385 455/39 |

OTHER PUBLICATIONS

DAIC "Patient Monitor Capable of Being Field Updated," http://www.dicardiology.com/tech/technology-integration-strategy-offers-remote-upgradability, Apr. 10, 2014, 1 page.

Kim et al., "Mobile Health Reference Architectures," Information Society (i-Society), 2013 International Conference on IEEE, Jun. 24-26, 2013, 7 pages.

Griscenko, Natalia, "Comparison and Evaluation of the Telehealth Systems Using a Discrete Event Simulation," Cranfield University School of Applied Sciences, MSc by Research Thesis, Oct. 2012, 151 pages.

Lin, M. K., "Evaluating the Acceptance of Mobile Technology in Healthcare: Development of a Prototype Mobile ECG Decision Support System for Monitoring Cardiac Patients Remotely," Dictoral dissertation, University of Southern Queensland, Feb. 2012, 226 pages.

International Search Report and Written Opinion in PCT/US2015/058334, dated Feb. 12, 2016, 12 pages.

* cited by examiner

WIRELESS AMBULATORY CARE NETWORK

BACKGROUND

Medical professionals input vital signs measurements into a patient's electronic medical record so they can be saved and used later. Many devices that can measure a patient's vital signs produce the measurement as an electronic signal. In order for a medical professional to enter recorded measurements into a patient's electronic medical record, the professional must remember and enter the measurements in a separate portal, such as a workstation computer.

The Bluetooth® wireless protocol enables devices with Bluetooth® radios to communicate information in a one-way or two-way exchange. Some medical devices have Bluetooth® radios. Many portable computing devices, such as laptop computers, smart phones and tablet computers also have Bluetooth® radios.

SUMMARY

In one aspect, a method for connecting with a wireless device is disclosed. The method can include receiving, at a host computing device, a Bluetooth® low-energy broadcast from one or more wireless devices that are in a range of the host computing device; identifying the one or more wireless devices; sorting the one or more wireless devices; displaying a name for each of the one or more wireless devices; and connecting to one of the one or more wireless devices.

The method can optionally include receiving a transmitter power from at least one of the one or more wireless devices, wherein the one or more wireless devices are sorted by the received transmitter power from at least one of the one or more wireless devices, determining the signal strength of the one or more wireless devices, receiving a transmitter power from at least one of the one or more wireless devices; and determining a distance of the one or more wireless devices from the host computing device using the signal strength and the transmitter power of the one or more wireless devices, wherein the one or more wireless devices are sorted using the distance from each wireless device to the host computing device. Additionally, the method can include pre-pairing the one or more wireless devices with the host computing device; setting a user-friendly alias that corresponds to the media access control (MAC) address of the one or more wireless devices; wherein the names displayed correspond to the user friendly alias of the one or more wireless devices; and wherein the name comprises up to 28 bytes. The one or more wireless devices can be sorted by the order in which the wireless devices were last connected to the host computing device. The method can also include pre-selecting one of the one or more wireless devices based on the wireless device most recently connected to the host computing device.

In a second aspect, a method for connecting to a host computing device is disclosed. The method can include activating a Bluetooth® low-energy radio of a wireless device, broadcasting a user-friendly name in one or more non-connectable undirected advertising events via the Bluetooth® low-energy radio, and forming a Bluetooth® Classic connection with the host computing device. Additionally, the method in this aspect can include broadcasting a transmitter power of the wireless device, wherein the user-friendly name comprises up to 28 bytes, pre-pairing the wireless device with the host computing device. The method in this aspect can also include deactivating the Bluetooth® low-energy radio, wherein the user-friendly name comprises up to 31 bytes.

In another aspect, a system for communicating vital signs data wirelessly is disclosed. The system can include a host computing device including non-transient storage media containing instructions stored thereon, where the instructions, when executed by one or more processors, cause the host computing device to receive a Bluetooth® low-energy broadcast from one or more electronic medical records portal computing devices; identify one or more electronic medical records portal computing devices that are in a range of the host computing device; sort the one or more electronic medical records portal computing devices; display a name for each of the one or more electronic medical records portal computing devices; and connect to one of the one or more electronic medical records portal computing devices; wherein the electronic medical records portal computing device includes non-transient storage media containing instructions stored thereon, where the instructions, when executed by one or more processors, cause the host computing device to: activate a Bluetooth® low-energy radio; broadcast a user-friendly name via the Bluetooth® low-energy radio; form a Bluetooth® Classic connection with the host computing device; and deactivate the Bluetooth® low-energy radio.

The system can also include a host computing device that is further configured to receive one or more vital sign measurements of a patient; and send the one or more vital sign measurements to the electronic medical records portal computing device, wherein the electronic medical records portal computing device is further configured to receive the one or more vital sign measurements from the host computing device. The electronic medical records portal computing device can be further configured to send one or more of the one or more vital sign measurements to an electronic medical record corresponding to the patient, wherein the host computing device disconnects from the electronic medical records portal computing device after sending the one or more vital sign measurements. The host computing device can further be configured to determine the signal strength of the one or more electronic medical records portal computing devices; receive a transmitter power from the electronic medical records portal computing device; and determine a distance of the electronic medical records portal computing device from the host computing device using the signal strength and the transmitter power of the one or more electronic medical records portal computing devices.

DETAILED DESCRIPTION

Examples of ambulatory care environments can include hospitals, clinics, managed care facilities, and other locations where medical care is provided. Medical personnel in ambulatory care environments can utilize vital sign monitoring devices, vital sign displays, personal computing devices and electronic medical record access portals. Medical staff and providers often need to record a patient's vital signs and enter those vital signs into the patient's electronic medical record. Currently, providers must perform vital sign measurements, remember the measurements, and then enter those measurements into one or more computing devices which may or may not be directly linked to the patient's electronic medical record.

The Bluetooth® Core Specification Version 4.0 introduced Bluetooth® Smart. Bluetooth® Smart is also known as Bluetooth® Low Energy Core Configuration. This document will refer to Bluetooth® Smart as Bluetooth® Low Energy, or BTLE. As of Version 4.0, there are three types of connections possible: (1) Bluetooth® "Classic", (2) Bluetooth® "High Speed", and (3) Bluetooth® Low Energy. The Bluetooth® Classic connection has remained essentially unchanged since Bluetooth® 2.1, with the same pairing and connection model.

Bluetooth® Low Energy uses a different radio than Bluetooth® Classic. Additionally, the pairing and connection models are different for Bluetooth® Low Energy than Bluetooth® Classic. Bluetooth® Low Energy can be used for shorter, more infrequent communication than Bluetooth® Classic. Additionally, Bluetooth® Low Energy, as the name implies, can use lower power than Bluetooth® Classic.

For the Bluetooth® devices described herein, "pairing" refers to the process of two devices meeting, where the devices are previously unknown to each other ("strangers"), using the "inquiry" process. "Discoverable" means a device is willing to form connections with strangers and is performing an "inquiry scan". "Discover" means a device is looking to form connections with strangers and is performing "inquiry". "Paired" means that a "pairing" process is complete: both devices in a connection are authenticated and share security information. "Bonded" means information obtained during the pairing process is stored in a "paired device list" (PDL) or a "trusted device list" (TDL), which can enable skipping the "pairing" process when the bonded devices are trying to connect.

"Connect" means communicate with known devices. "Connecting" means looking to communicate with known devices, which can follow immediately after "pairing". "Connectable" means a device is willing to form connections with known devices, which can be stored in a PDL. "Connected" means two devices are able to exchange data. "Disconnect" means to stop communication and break the "connection".

Figure 1:
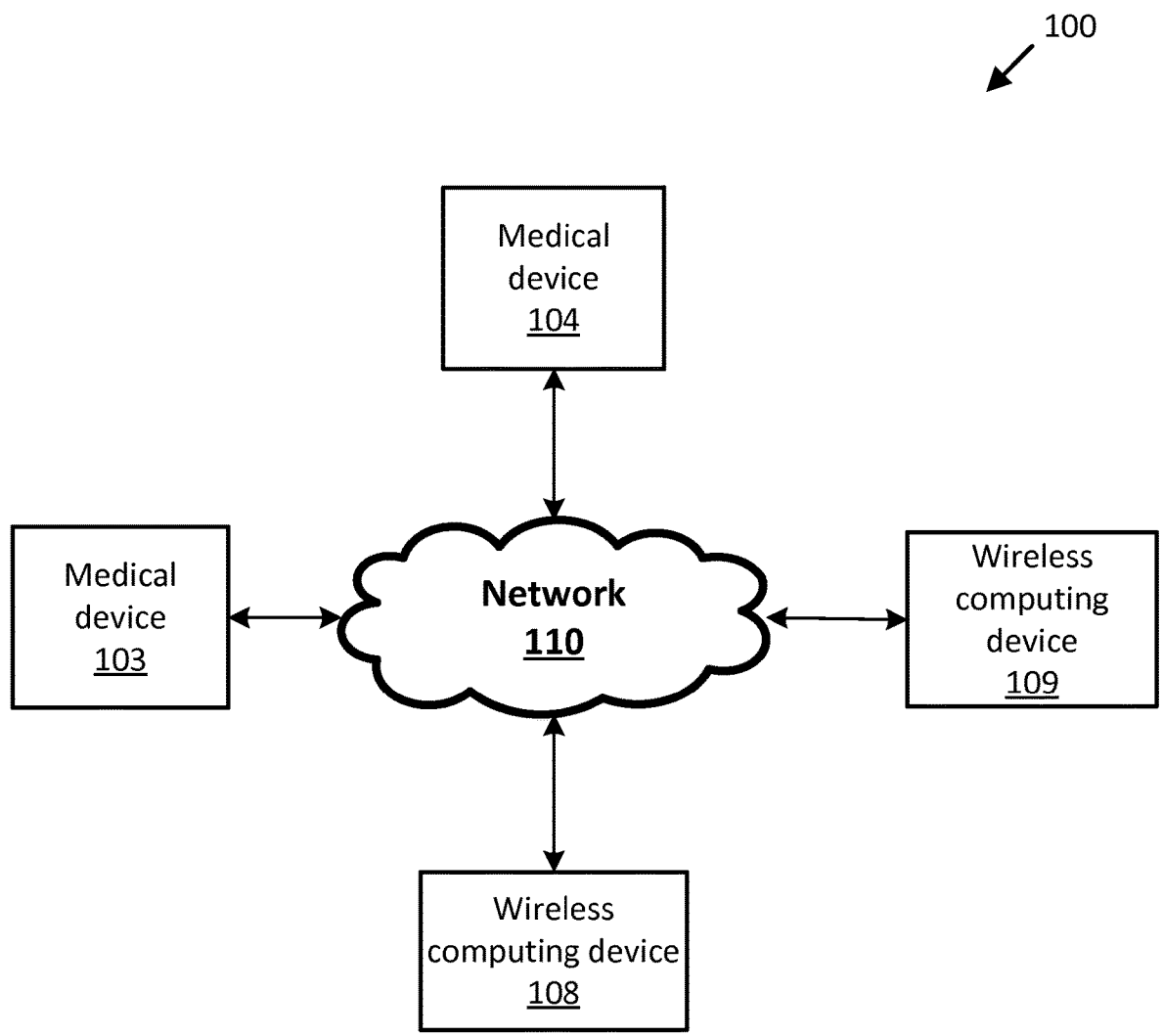
FIG. 1 illustrates a block diagram of a wireless ambulatory care system.

FIG. 1 illustrates a block diagram of an example wireless ambulatory care network 100. The example network 100 includes medical devices 103 and 104, wireless computing devices 108 and 109, and communication network 110. In embodiments, the example network 100 can include more or fewer medical devices 103 and 104. In embodiments, the example network can include more or fewer wireless computing devices 108 and 109. The communication network 110 can be a wireless network, such as WiFi, Bluetooth, Zigbee, Ant, Z-Wave, etc.

In some embodiments, the one or more medical devices 103 and 104 can include one or more vital sign measurement components. For example, the medical devices 103 can include, for example, a thermometer, a heart rate monitor, a pulse oximeter, a non-invasive blood pressure monitor, and a respiration rate monitor. In embodiments, one or more vital sign measurement components are wirelessly linked to the medical devices 103 and 104 and can transmit measurements to the medical devices 103 and 104.

The one or more medical devices 103 and 104 have hardware and software components that support Bluetooth® Low Energy. Example medical devices 103 and 104 are depicted and described in more detail with reference to FIGS. 2-5, below. Example computing components of medical devices 103 and 104 are shown and described in more detail with reference to FIG. 7, below.

In some embodiments, the one or more wireless computing devices 108 and 109 can be smart phones, tablet computers, personal digital assistants, laptop computers, and desktop computers, which can optionally be mounted on portable carts. Example computing components of the one or more wireless computing devices 108 and 109 are shown and described in more detail with reference to FIG. 7, below. The use of less complicated wireless computing devices 108 and 109, such as heart rate monitors, pulse oximeters, etc., is also contemplated by this document.

Figure 2:
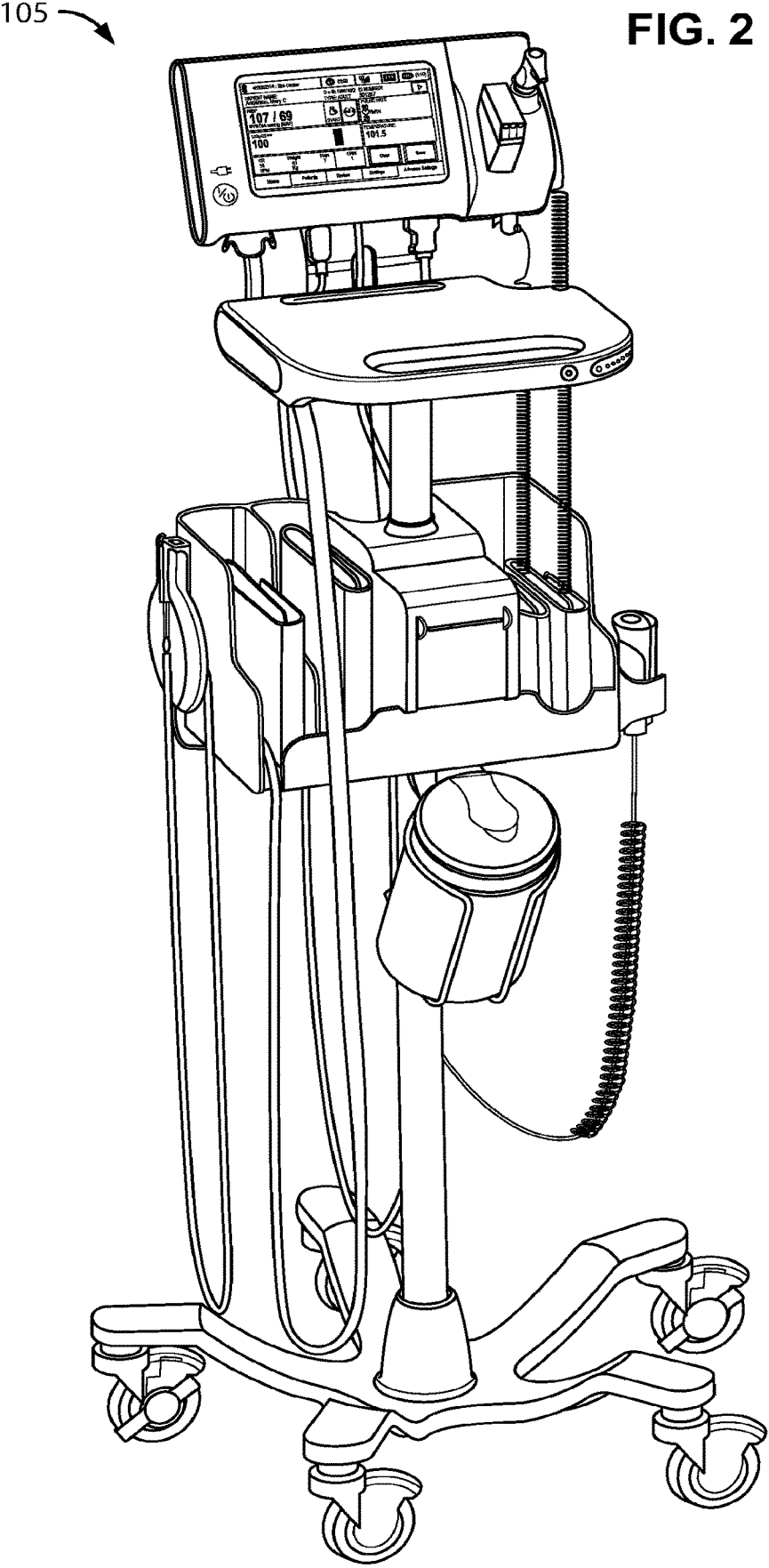
FIG. 2 illustrates an example medical device of the system of FIG. 1.
Figure 3:
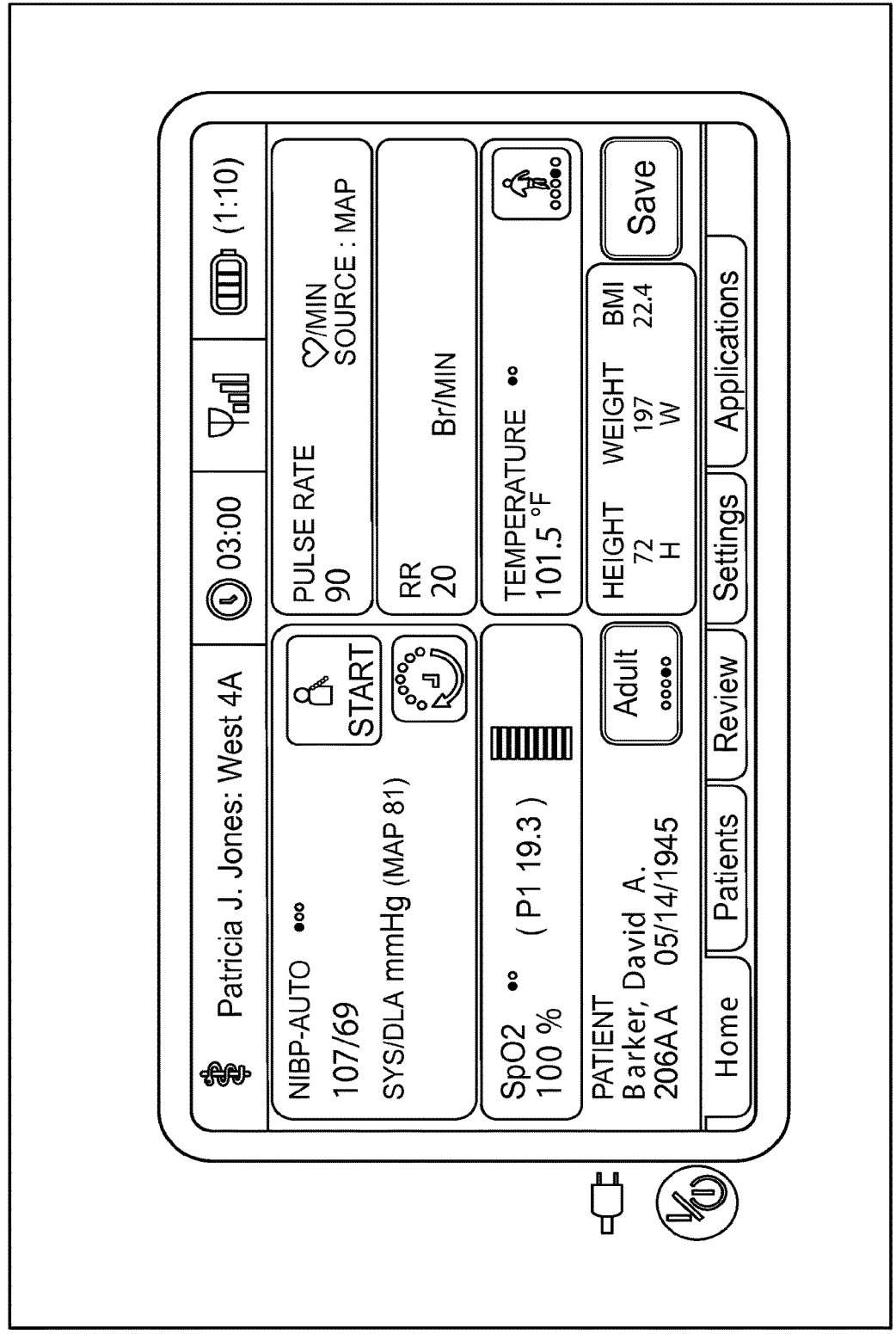
FIG. 3 illustrates another example medical device of the system of FIG. 1.

FIG. 2 illustrates one example of the medical device 105. The medical device 105 is shown on a mobile cart, and the medical device 105 is programmed to provide the functionalities described herein. The medical device 105 includes a user interface, such as a touch screen, and includes the ability to execute multiple workflows or profiles. In some embodiments, the medical devices 105 and 106 in FIGS. 2 and 3 are the medical device 103 or 104 shown in, and described with reference to, FIG. 1. Other embodiments can include more or fewer components than those shown in FIG. 2, or include different components that accomplish the same or a similar function.

The medical device 105 is able to operate within one or more profiles. A profile is a series of one or more tasks that a user of the medical device 105 performs. When the medical device 105 operates within a profile, the medical device 105 provides functionality suitable for assisting the user in performing the profile. When the medical device 105 operates within different profiles, the medical device 105 provides different functionality.

When the medical device 105 is manufactured, the medical device 105 is configured to be able to operate within one or more profiles. After the medical device 105 is manufactured, the medical device 105 can be reconfigured to operate within one or more additional profiles. In this way, a user can adapt the medical device 105 for use in different profiles as needed.

In various embodiments, the medical device 105 operates within various profiles. For example, in some embodiments, the medical device 105 can operate within a monitoring profile or a non-monitoring profile. Example types of non-monitoring profiles include, but are not limited to, a spot check profile and an office profile. An example of a monitoring profile includes, but is not limited to, an intervals profile.

An additional example of the medical device 106 is shown in FIG. 3. In this example, the medical device 106 is similar to that of the medical device 105 described above. In embodiments, the medical device 106 is mounted on a wall. The medical device 106 is programmed in a manner similar to that described above to monitor physiological parameters of a patient. In some embodiments, the medical device 106 is a stand-alone device, which can mean that is not part of a mobile cart and it is not part of a wall-mounted station.

The example medical devices 105 and 106 can be provided with hardware enabling Bluetooth® Classic, Bluetooth® High Speed and Bluetooth® Low Energy connections. The example medical devices 105 and 106 communicating via Bluetooth® Classic can send data using the radio frequency communication (RFCOMM) transport protocols with a custom Universally Unique Identifier (UUID). The custom UUID can prevent the example medical devices 105 and 106 from connecting to any device. Additionally, the custom UUID can make it easier for the wireless computing devices 108 and 109 to discover and connect to the example medical devices 105 and 106. Generally, wireless computing devices that support "classic" Bluetooth® 2.1 and above also support RFCOMM. In particular, iPads® and iPhones® require an authentication coprocessor for applications to receive RFCOMM data, as well as a special protocol named iAP.

Figure 4:
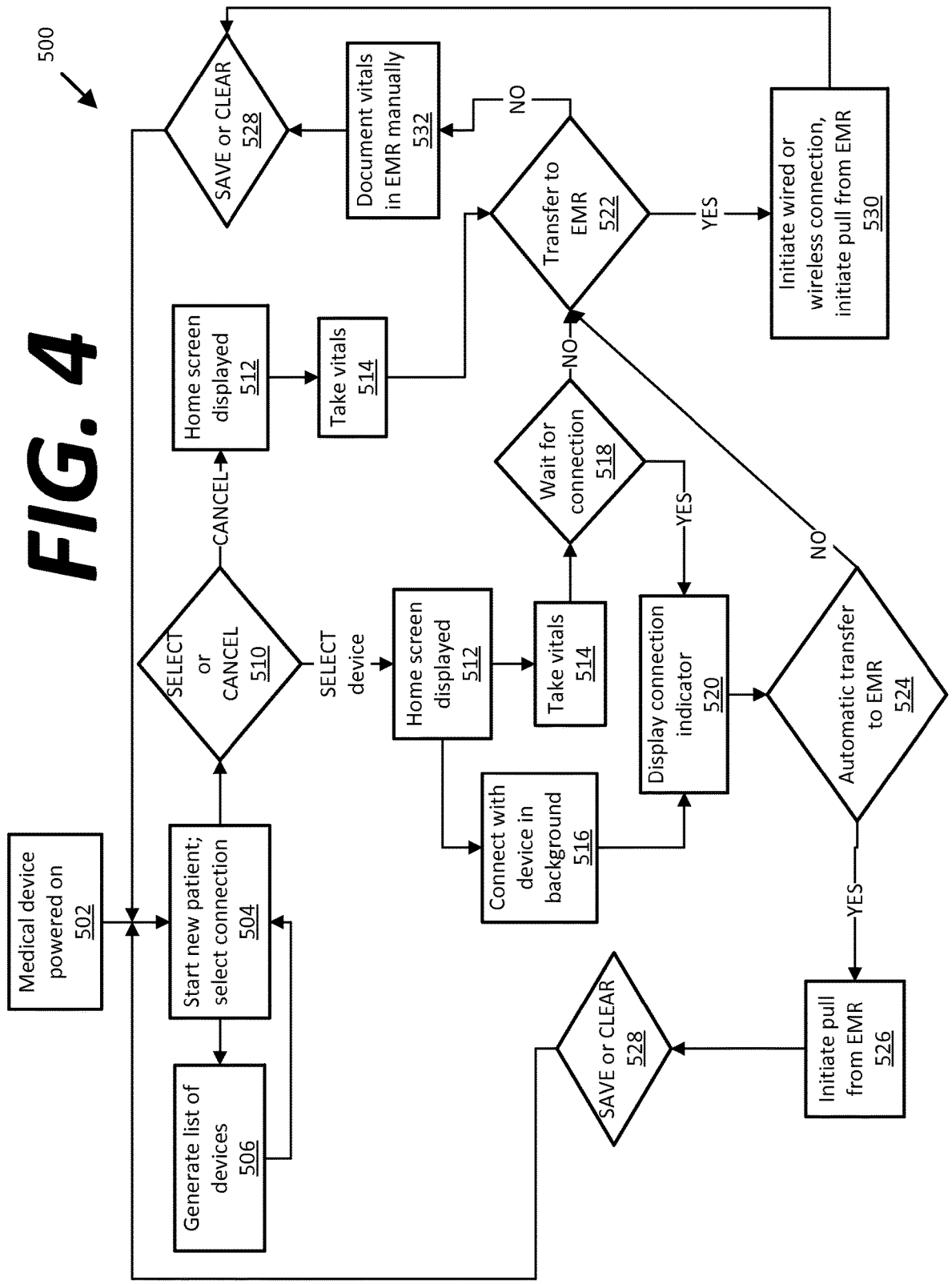
FIG. 4 is a flow chart illustrating an example method for using the example wireless ambulatory care system.

FIG. 4 is a flowchart of an example use 500 of the exemplary wireless ambulatory care network 100. The example use 500 can include powering on the medical device (step 502), starting a new patient and selecting a connection (step 504), generating a list of wireless computing devices (step 506), determining whether to select or cancel (step 510), displaying the home screen (step 512), taking vitals (step 514), connecting with a device in the background (step 516), waiting for a connection (step 518), displaying a connection indicator (step 520), decision whether to transfer to EMR (step 522), decision whether to automatically transfer to EMR (step 524), initiate transfer to EMR (step 526), save or clear decision (step 528), initiate connection and transfer to EMR (step 530), and document vitals in EMR manually (step 532). Example medical devices 103, 104, 105 and 106 described above can be used in example use 500. Example wireless computing devices 108 and 109 can be used in example use 500. Other embodiments may exclude some or all of these steps or add additional steps.

In an embodiment, the medical devices used in the example method 500 are pre-paired with the wireless computing devices. That is, when a user begins method 500, their wireless computing device has already been paired and/or bonded with some or all of the example medical devices in the facility. In some embodiments, the wireless computing devices that have been bonded with the medical devices comprise an "approved" device list.

Possible advantages of pre-pairing the medical devices with the wireless computing devices include that the user does not need to perform the pairing process each time they see a new patient, and that the user does not need to wait for the pairing process to finish. The pre-configuration of the medical devices and the wireless computing devices is described in more detail with reference to FIG. 5, below.

In this embodiment, the use begins by powering on the medical device (step 502). A nurse, provider, facility staff, or other personnel may perform this step in various embodiments (collectively, the "user"). For the embodiments where the medical device is mobile, this step may also include the user physically moving the medical device into the patient's room, if it is not already in the patient's room. Additionally, this step can include activating the Bluetooth® radio or radios in the medical device.

Once the medical device is powered on, the user can start a new patient and select a connection (step 504) via the medical device's user interface. Starting a new patient can optionally include entering the patient's name. In embodiments, at step 504 the medical device creates a new entry in a database, stored locally or in the cloud, for the new patient.

In embodiments, after the user selects "start new patient" (or an equivalent variation thereof), the medical device can begin to generate a list of devices (step 506). In some embodiments, the medical device uses a static or fixed list and does not generate a list of devices when the user selects "start new patient." Step 506 is shown and described in more detail with reference to FIG. 5, below.

Select connection (step 504) can present the user with one or more wireless computing devices that resulted from the generating a list of devices operation (step 506). In embodiments, the medical device lists the approved wireless computing devices as they are discovered. As discussed in more detail below with reference to FIGS. 7 and 8, the list can be sorted alphabetically, in order of use, or by distance from the medical device. In embodiments, the order of use is a frequency algorithm that stores how often a connection has been made with a particular computing device.

Figure 6:
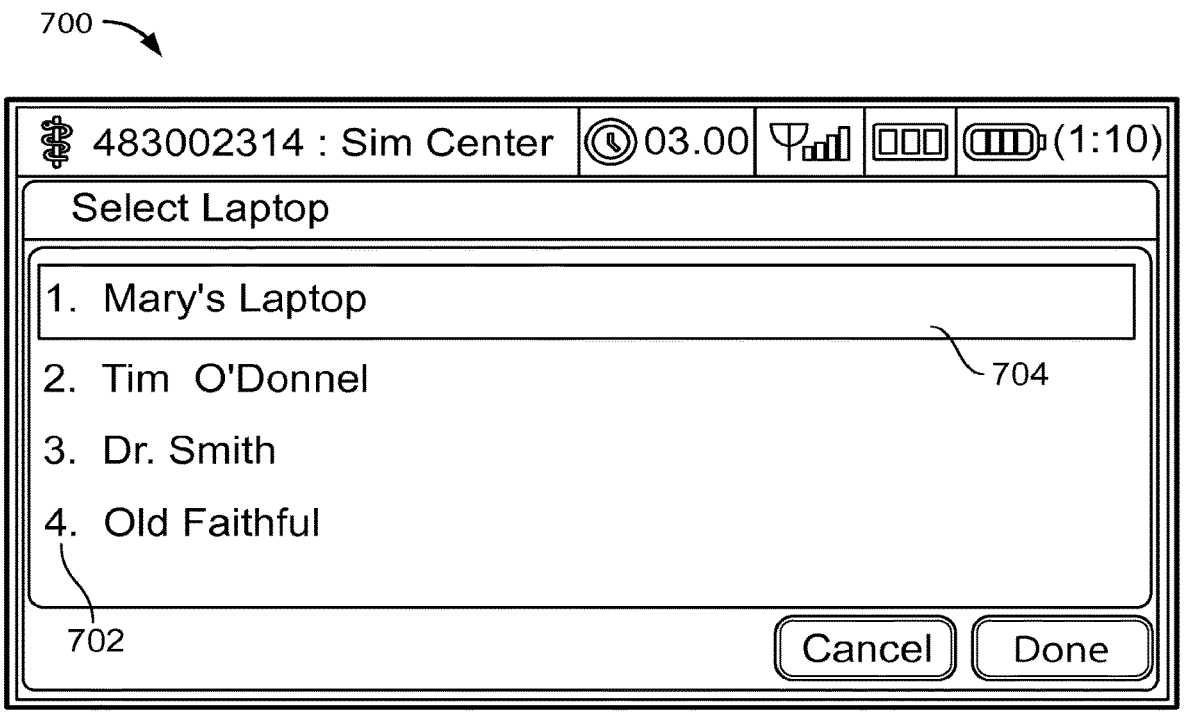
FIG. 6 illustrates an example user interface for selecting a wireless computing device.

In embodiments, the user can request that the list of wireless computing devices be refreshed, which initiates step 506 again. In embodiments, the user can select a wireless computing device via a touchscreen on the medical device or via buttons on the medical device's housing. An example user interface showing a list of wireless computing devices in range of a medical device is shown in FIG. 6.

In some embodiments, the user will have a laptop or tablet computer, for example, that is wirelessly connected to an electronic medical record system. In embodiments, these wireless computing devices are pre-paired with one or more of the medical devices. Additionally, the wireless computing device can broadcast a friendly name, as discussed above.

After populating the list of wireless computing devices, the user can either select one of the displayed devices or cancel the connection process (step 510). In embodiments, the dialogue remains on the medical device's display until the user selects a device or chooses CANCEL. In embodiments, if only one wireless computing device is within range of the medical device, that wireless computing device is highlighted in the list by default. In embodiments, if multiple approved wireless computing devices are within range of the medical device, then the wireless computing device that is calculated as being the closest can be highlighted by default.

If the user selects CANCEL, then the dialogue closes. The use 500 can continue without a connection being formed with the wireless computing devices shown in the list. In embodiments, the user can return to step 506 later in the use and generate a list of devices after selecting CANCEL.

If the user selects CANCEL, then the medical device can display the home screen on the user interface (step 512). If the user chooses a wireless computing device using SELECT, the medical device can display the home screen on the user interface (step 512). That is, in some embodiments, the same or a similar home screen is displayed regardless whether the user decided to SELECT a device or CANCEL the connection.

If the user highlights a wireless computing device and chooses SELECT, then the medical device closes the dialogue. The medical device and wireless computing device can continue the connecting (or pairing) process in the background (step 516) while the user records vital sign measurements (step 514). In some embodiments, the vital sign measurements are communicated from one or more measurement devices to the medical device via a wired or wireless connection.

In embodiments, the connection between the medical device and the wireless computing device is not complete by the time the user finishes taking the patient's vitals (step 514). The medical device can present a dialogue prompting the user whether to wait for the connection to be complete (step 518). If the user chooses YES, then the medical device can display a visible connection indicator, and/or emit a sound, that indicates the pairing process is complete (step 520). If the user chooses NO, then the use 500 proceeds to the transfer to EMR step (step 522).

Once the medical device and wireless computing device have completed pairing, both devices can switch to Bluetooth® Classic radio to achieve faster data transfer rates. One exception is that connections between a medical device and an Apple® iPad® will remain over Bluetooth® Low Energy.

After the medical device and wireless computing device are paired, a dialogue can appear on either or both devices prompting the user whether to transfer the vital signs to the patient's EMR (step 524). If the user chooses NO, then the use 500 proceeds to the transfer to EMR step (step 522). If the user chooses YES, then the vital sign data are transferred to the wireless computing device, which transfers the data to the patient's EMR (step 526). In some embodiments, the wireless computing device has been configured to send data to the patient's EMR before receiving the data from the medical device. Alternatively, in some embodiments, the wireless computing device can prompt the user to enter identifying information for the patient's EMR after receiving the data from the medical device.

In some embodiments, the system is pre-configured to automatically transfer the vital sign data to the patient's EMR without prompting the user (omitting step 524). In those embodiments, the vital sign data are transferred to the patient's EMR as soon as the medical device receives the measurements and communicates those measurements to the wireless computing device.

Referring again to the decision in step 522, no connection exists between the medical device and a wireless computing device. Thus, at step 522 the recorded vital sign data are not available for wireless transfer to the EMR. However, if the user wants to send the data to the EMR, the user can initiate a transfer to the EMR via a wired connection (step 530), such as a universal serial bus (USB) connection. Alternatively, the user can enter the vital sign measurements into the patient's EMR manually (step 532).

After the data are transferred to the patient's EMR in step 526 or step 530, the user can select SAVE or CLEAR (step 528) on the medical device. Similarly, after the user has manually entered the vital sign data into the patient's EMR in step 532, the user can select SAVE or CLEAR (step 528) on the medical device. Pressing SAVE in step 528 will cause the patient's data to be stored in the medical device's memory and then initiate the start new patient dialogue (step 504). Pressing CLEAR will clear the data and initiate the start new patient dialogue (step 504).

At the finish of use 500, the user can repeat the process with another patient. In some embodiments, the user would return the medical device to a central location or hallway and take their wireless computing device with them to the next patient's room, where they can repeat the connection process with the same or a different medical device.

Figure 5:
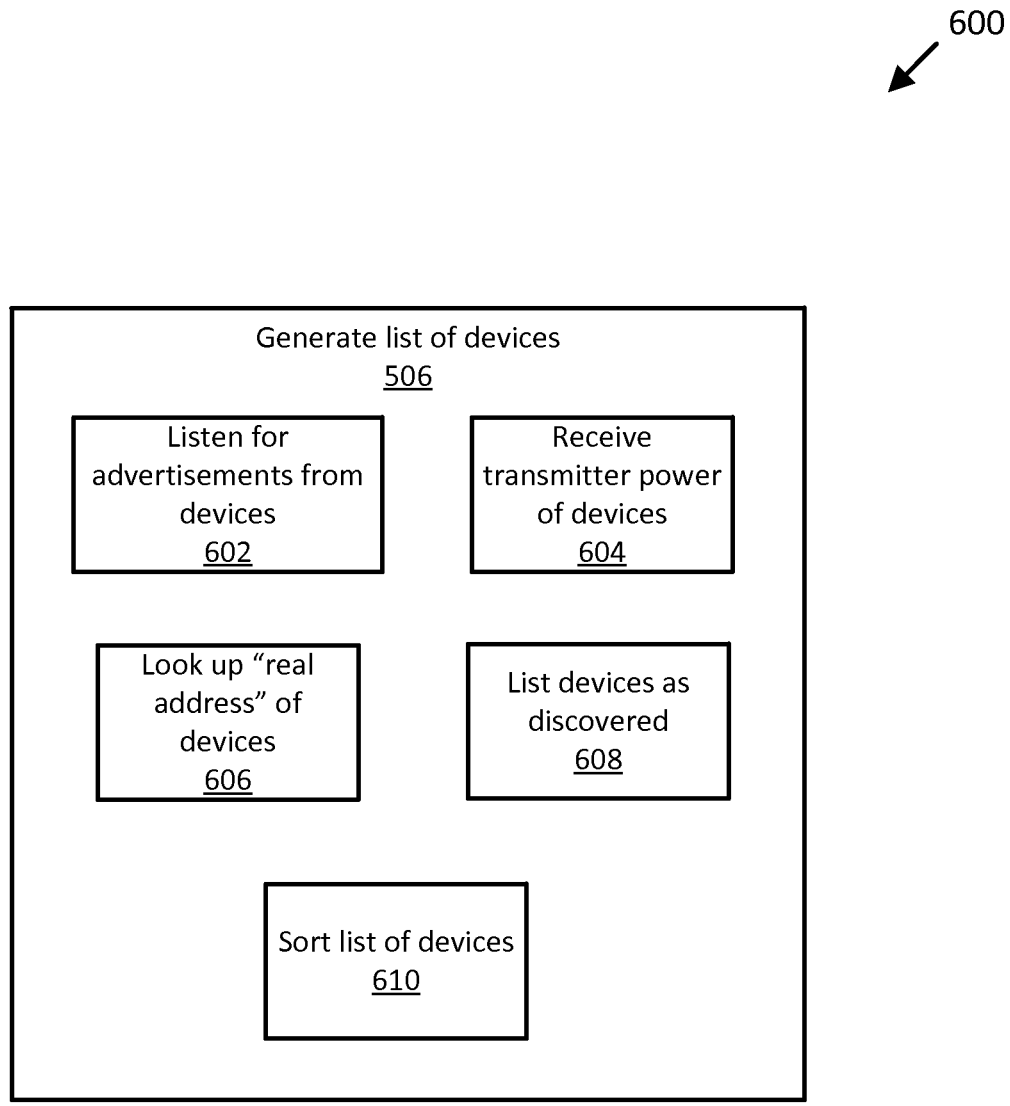
FIG. 5 is a block diagram illustrating example components of generating a list of wireless computing devices.

FIG. 5 is a block diagram illustrating example actions 600 comprising the generate list of devices step (step 506). The example actions include listen for advertisements from wireless computing devices 602, receive the transmitter power of wireless computing devices 604, look up "real address" of wireless computing devices 606, list devices as discovered 608, and sort list of wireless computing devices 610. Other embodiments may exclude some or all of these actions or add additional actions.

Generate list of devices (step 506) can include listening for advertisements from wireless computing devices 602. In these embodiments, the medical device can be considered an "initiator" because the medical device is looking to form a connection to another device. The wireless computing devices can be configured to transmit advertising packets on the advertising channels.

In embodiments, some or all of the wireless computing devices have been paired and/or bonded with some or all of the medical devices before the user's use 500 begins. In embodiments, a configuration file stored on the medical device contains an approved list of wireless computing devices the medical device is allowed to pair with. In an embodiment, if the configuration file does not list any wireless computing devices, then the medical device searches for all Bluetooth® devices within range. In an embodiment, if the configuration file lists specific wireless computing devices, then the medical device searches only for those devices. In some embodiments, the pairing and/or bonding was performed between the medical device and each wireless computing device separately and before example use 500, for example by a technician.

In embodiments, if the configuration file lists approved wireless computing devices, then a configuration tool can also allow a user to manually input a name or label to display when the medical device detects that wireless computing device. These names can be termed "user-friendly" or an "alias." For instance, a given wireless computing device might be a laptop with media access control (MAC) address xx-xx-xx-xx-xx-xx, but the medical device displays "Amy's Laptop."

In some embodiments, the wireless computing devices are pre-programmed to broadcast a "user-friendly name" of the device in the non-directed advertisements. Broadcast, as used herein, can mean to send data in "non-connectable undirected advertising events". The broadcast can be advertised over 1 to 3 radio frequency channels, which can be selected during the device's configuration. The time between broadcasts, also known as the advertising interval, can be from 20 ms to 10.24 s; from 100 ms to 5 s; from 50 0 ms to 2 s; from 250 ms to 1 s; from 1 s to 3 s; or from 750 ms to 1.5 s. In embodiments, the broadcast does not include the MAC address of the wireless computing device.

In embodiments, the user-friendly name can be up to 248 bytes long. In embodiments, the wireless computing device is programmed to broadcast a "user-friendly name" of up to 32 bytes or of up to 31 bytes. In other embodiments, the user-friendly name is limited to a maximum of 28 bytes. In those embodiments, the broadcast can include the transmitter power of the Bluetooth® radio. As an example, a wireless computing device is named "Jonathan James Doeington's Laptop," which contains 33 characters. If the broadcast limit is 28 bytes, the wireless computing device could broadcast a truncated version, such as "Jonathan James Doeington," or an abbreviated version, such as "J. J. Doeington's Laptop".

Using Bluetooth® Classic to scan for wireless computing devices has drawbacks over the instantly disclosed methods that employ Bluetooth® Low Energy. For instance, Bluetooth® Classic does not provide a way for the medical device to discover which wireless computing devices are in range without attempting to connect to every device in the paired device list. Because the medical device will initiate the connection, the medical device expects the wireless computing devices to be connectable. Connectable devices do not transmit; rather, they wait for the connecting device to page them. In other words, the proximity determination, described in more detail below, could not occur without the medical device connecting to each device in range that is listed in the paired device list.

Detecting connection failures attributable to a device being out of range can take 5 to 10 seconds. If there are twelve or more wireless computing devices in the paired device list, then the detection of all devices within range could take two minutes. Such a long wait is undesirable.

Additionally, using the discoverable functionality in Bluetooth® Classic is less advantageous than the instant method. Using the discoverable functionality would require the wireless computing devices to be discoverable all the time. The medical device would perform inquiry to find all devices in range. This can be slow, as discovery can take 30 seconds or more by the time every friendly name is fetched. Also, this could be dangerous, as a bad actor could find the wireless computing device and attempt to pair with the device using "Just Works" pairing.

In the embodiment where the wireless computing device does not support Bluetooth® Low Energy and just Bluetooth® Classic, the medical device can be configured to display the entire paired device list. The list can be sorted by friendly name and the user can scroll through the list to find their wireless computing device. In these embodiments, the medical device does not need to attempt to discover or connect with each device, which can be time-consuming and undesirable.

Generating the list of devices (step 506) can also include receiving the transmitter power of the devices 604. As discussed above, the wireless computing devices can be configured to transmit their Bluetooth® radio transmitter power in the advertising packets. Additionally, the medical device can be configured to read the received signal strength indication (RSSI). In embodiments, the medical device can use the RSSI in sorting the device list 610. In other embodiments, the medical device can use both the transmitter power and the RSSI in sorting the device list 610. Using both the transmitter power and the RSSI can produce a more accurate assessment of the proximity of each detected wireless device relative to the other detected devices.

Additionally, generating the list of devices (step 506) can include looking up the "real address" of one or more wireless computing devices 606. In embodiments, the wireless computing devices are configured to broadcast "user-friendly" names in the advertising broadcasts instead of their MAC address. In those embodiments, the medical device has a list associating the "user-friendly" names of wireless computing devices with their MAC or "real" address.

During step 506, the user interface can display the devices as they are discovered 608. In some embodiments, the wireless computing device that is closest to the medical device, which can be the user's wireless computing device, is discovered first. In those embodiments, this functionality enables the user to quickly select their wireless computing device for pairing.

In embodiments, the medical device can be configured to sort the list of devices 610. In some embodiments, the medical device sorts the devices by proximity. The proximity determination can include the signal strength of each wireless computing device or the signal strength of each wireless computing device and the transmitter power of each wireless computing device. In some embodiments, the medical device sorts the devices alphabetically.

In some embodiments, the medical device sorts the devices in order of use, with the devices paired-with most often listed at the top. In those embodiments, wireless computing devices that have paired with the medical device an equal number of times can be sorted by the last time the pairing occurred, with the most recently-connected wireless computing device being listed first. For example, if Dr. Smith paired a computing device with the medical device first, then Dr. Smith would be listed first for the next (second) user, Dr. Jones. If Dr. Jones then uses it third, Dr. Jones would be listed first because although Dr. Smith and Dr. Jones have each paired with the device once, Dr. Jones was the most recent. In embodiments, the list of recently-paired devices is cleared at given intervals, such as, for example, every 1 hour, every 2 hours, every 4 hours, every 8 hours, every 10 hours, every 12 hours, and every 24 hours.

FIG. 6 depicts an example user interface 700 displaying a list of discovered devices. The example user interface 700 can be displayed by a medical device. The example user interface 700 can correspond to the select connection step (step 504) in example use 500, shown in FIG. 4 and described in more detail above. In the example user interface 700, a list 702 of wireless computing devices is shown and one of the wireless computing devices is pre-selected 704, as shown by highlighting. Other embodiments can include more or fewer icons in the display, and the icons can have different names or depictions. Also, other embodiments can include more or fewer discovered wireless computing devices.

In embodiments, the example user interface 700 can display the wireless computing devices as they are discovered. In some embodiments, the user interface 700 can include an icon, such as an hour glass, indicating that the medical device is still populating the device list 702. In example user interface 700, "Mary's Laptop" is preselected 704 and is listed as the first of four discovered devices. The list 702 can be sorted according to the methods described with reference to sort list of devices 610 with reference to FIG. 5, above.

In embodiments, the user selects a highlighted wireless computing device 704 using directional arrows or by touching the medical device screen and selecting DONE (or OK, SELECT, etc.). In some embodiments, after the user chooses a wireless computing device, the pairing process commences in the background and the medical device user interface can display a home screen or a record vitals screen.

Figure 7:
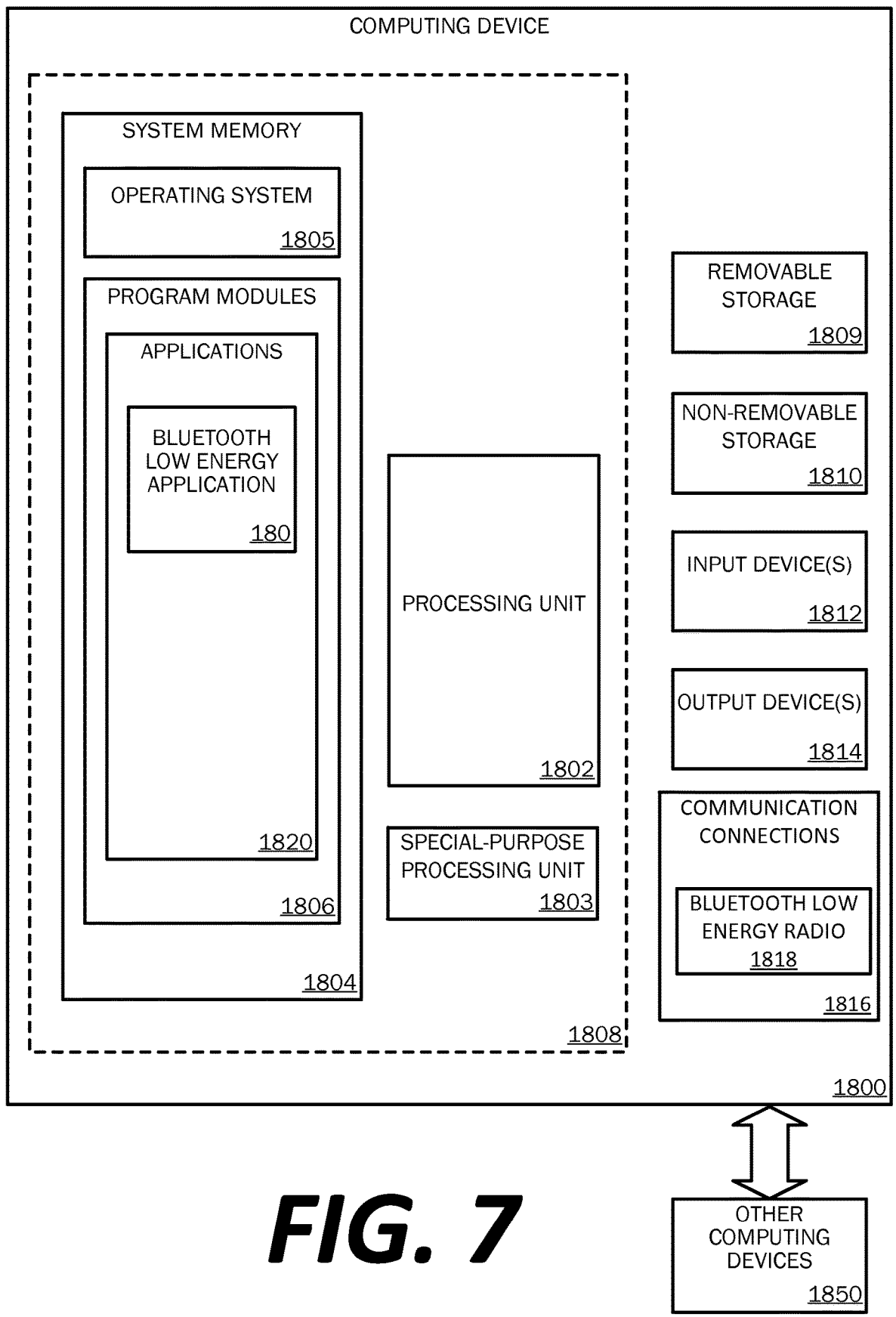
FIG. 7 is a block diagram illustrating physical components of a computing device with which examples and embodiments of the disclosure can be practiced.

FIG. 7 is a block diagram illustrating physical components (i.e., hardware) of a computing device 1800 with which embodiments of the disclosure may be practiced. The computing device components described below may be suitable to act as the computing devices described above, such as wireless computing device and/or medical device of FIG. 1. In a basic configuration, the computing device 1800 may include at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820 such as the Bluetooth Low Energy Application 180. The operating system 1805, for example, may be suitable for controlling the operation of the computing device 1800. Furthermore, embodiments of the disclosure may be practiced in conjunction with a graphics library, other operating systems, or any other application program and is not limited to any particular application or system. This basic configuration is illustrated in FIG. 7 by those components within a dashed line 1808. The computing device 1800 may have additional features or functionality. For example, the computing device 1800 may also include additional data storage devices (removable and/or non-removable) such as, for example, magnetic disks, optical disks, or tape. Such additional storage is illustrated in FIG. 7 by a removable storage device 1809 and a non-removable storage device 1810.

As stated above, a number of program modules and data files may be stored in the system memory 1804. While executing on the processing unit 1802, the program modules 1806 (e.g., Bluetooth Low Energy Application 180) may perform processes including, but not limited to, generate list of devices, broadcast user-friendly name, broadcast transmitter power, determine proximity of wireless computing device, connect with wireless computing device, transfer vital sign data to a patient's EMR, sort list of wireless computing devices within range, and other processes described with reference to the figures as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 7 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, with respect to the Bluetooth Low Energy Application 180 may be operated via application-specific logic integrated with other components of the computing device 1800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1800 may also have one or more input device(s) 1812 such as a keyboard, a mouse, a pen, a sound or voice input device, a touch or swipe input device, etc. The output device(s) 1814 such as a display, speakers, a printer, etc. may also be included. The aforementioned devices are examples and others may be used. The computing device 1800 may include one or more communication connections 1816 allowing communications with other computing devices 1818. Examples of suitable communication connections 1816 include, but are not limited to, RF transmitter, receiver, and/or transceiver circuitry; universal serial bus (USB), parallel, and/or serial ports. Additionally, the communication connections 1816 can include a Bluetooth Low Energy Radio.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Embodiments of the present disclosure may be utilized in various distributed computing environments where tasks are performed by remote processing devices that are linked through a communications network in a distributed computing environment.

The flow diagrams depicted herein are just examples. There may be many variations to these diagrams or the steps (or operations) described therein without departing from the spirit of the disclosure. For instance, the steps may be performed in a differing order, or steps may be added, deleted or modified.

While embodiments have been described, it will be understood that those skilled in the art, both now and in the future, may make various improvements and enhancements can be made.

What is claimed is:

1. A method for connecting with a wireless device, comprising:
   receiving, on a host medical computing device, a selection to start a new patient;
   receiving, at the host medical computing device, a broadcast from one or more wireless devices that are in a range of the host medical computing device;
   identifying the one or more wireless devices;
   sorting the one or more wireless devices;
   displaying a name for each of the one or more wireless devices on a device selection display on the host medical computing device based on an approved list of wireless devices contained in a configuration file stored on the host medical computing device;
   highlighting one wireless device from the one or more wireless devices displayed on the device selection display of the host medical computing device; and
   as a background process on the host medical computing device, connecting to one of the one or more wireless devices, including:
   closing the device selection display;

recording vital sign measurements while connecting to the one or more wireless devices;

transferring the vital sign measurements to the connected wireless device; and using the connected wireless devices to transfer the vital signs to an electronic medical record stored in a electronic medical record system.

2. The method for connecting with a wireless device of claim 1, further comprising receiving a transmitter power from at least one of the one or more wireless devices.

3. The method for connecting with a wireless device of claim 2, wherein the one or more wireless devices are sorted by the transmitter power received from at least one of the one or more wireless devices.

4. The method for connecting with a wireless device of claim 1, further comprising:

determining a signal strength of the one or more wireless devices.

5. The method for connecting with a wireless device of claim 4, further comprising:

receiving a transmitter power from at least one of the one or more wireless devices; and determining a distance of the one or more wireless devices from the host medical computing device using the signal strength and the transmitter power of the one or more wireless devices.

6. The method for connecting with a wireless device of claim 5, wherein the one or more wireless devices are sorted using the distance from each wireless device to the host medical computing device.

7. The method for connecting with a wireless device of claim 1, further comprising:

pre-pairing the one or more wireless devices with the host medical computing device.

8. The method for connecting with a wireless device of claim 7, further comprising:

setting a user-friendly alias that corresponds to a media access control (MAC) address of the one or more wireless devices;

wherein the names displayed correspond to a user friendly alias of the one or more wireless devices; and wherein the name comprises up to 28 bytes.

9. The method for connecting with a wireless device of claim 1, wherein the one or more wireless devices are sorted by an order in which the wireless devices were last connected to the host medical computing device; and further comprising pre-selecting one of the one or more wireless devices based on the wireless device most recently connected to the host medical computing device.

10. A system for communicating vital signs data wirelessly, comprising:

a host medical computing device including:

one or more processors; and memory storing instructions that, when executed by the one or more processors, cause the host medical computing device to:

receive a selection to start new patient;

receive a broadcast from one or more electronic medical records portal computing devices, the one or more electronic medical records portal computing devices being connected to an electronic medical record system;

identify one or more electronic medical records portal computing devices that are in a range of the host medical computing device;

sort the one or more electronic medical records portal computing devices;

on a device selection display, display a name for each of the one or more electronic medical records portal computing devices based on an approved list of wireless devices contained in a configuration file stored on the host medical computing device, and wherein a configuration tool allows manual input of a name to display on the host medical computing device for an identified electronic medical records portal computing device;

highlighting a closest in proximity of the one or more electronic medical records portal computing devices on the device selection display; and as a background process, connect to one of the one or more electronic medical records portal computing devices, including:

closing the device selection display;

recording vital sign measurements while connecting to the one or more electronic medical records portal computing devices;

transferring the vital sign measurements to the one or more electronic medical records connected portal computing devices; and using the one or more electronic medical records connected portal computing devices to transfer the vital signs to an electronic medical record stored in the electronic medical record system.

11. The system for communicating vital signs data wirelessly of claim 10, wherein the electronic medical records portal computing device includes:

one or more portal computing device processors;

portal computing device memory storing instructions that, when executed by the one or more portal computing device processors, cause the electronic medical records portal computing device to:

activate a Bluetooth® low-energy radio;

broadcast a user-friendly name via the *Bluetooth*® low-energy radio;

form a Bluetooth® Classic connection with the host medical computing device; and deactivate the Bluetooth® low-energy radio.

12. The system for communicating vital signs data wirelessly of claim 11, wherein the host medical computing device is further programmed to send the vital sign measurements to the electronic medical records portal computing device; and wherein the electronic medical records portal computing device is further programmed to receive the vital sign measurements from the host medical computing device.

13. The system for communicating vital signs data wirelessly of claim 12, wherein the electronic medical records portal computing device is further programmed to send one or more of the vital sign measurements to an electronic medical record corresponding to a patient.

14. The system for communicating vital signs data wirelessly of claim 13, wherein the host medical computing device disconnects from the electronic medical records portal computing device after sending the vital sign measurements.

15. The system for communicating vital signs data wirelessly of claim 11, wherein the host medical computing device is further programmed to:

determine a signal strength of the one or more electronic medical records portal computing devices;

receive a transmitter power from the electronic medical records portal computing device; and determine a distance of the electronic medical records portal computing device from the host medical computing device using the signal strength and the transmitter power of the one or more electronic medical records portal computing devices.

16. A method for connecting to a host medical computing device, comprising:

activating a Bluetooth® low-energy radio of a wireless device;

broadcasting a user-friendly name in one or more non-connectable undirected advertising events via the Bluetooth® low-energy radio, the user-friendly name identifying the wireless device;

forming a Bluetooth® Classic connection with the host medical computing device when the user-friendly name corresponds to a name on an approved list of wireless devices contained in a configuration file stored on the host medical computing device;

while forming the Bluetooth® Classic connection, as a background process, receiving vital sign measurements from the host medical computing device, the vital sign measurements being associated with a new patient selected by the host medical computing device;

connecting to an electronic medical record system;

transferring the vital sign measurements to an electronic medical record in the electronic medical record system; and storing the electronic medical record in the electronic medical record system.

17. The method for connecting to a host medical computing device of claim 16, further comprising:

broadcasting a transmitter power of the wireless device.

18. The method for connecting to a host medical computing device of claim 17, wherein the user-friendly name comprises up to 31 bytes.

19. The method for connecting to a host medical computing device of claim 18, further comprising pre-pairing the wireless device with the host medical computing device.

20. The method for connecting to a host medical computing device of claim 16, further comprising deactivating the Bluetooth® low-energy radio.

* * * * *